United States Patent [19]

Dassanayake et al.

[11] Patent Number: 5,573,726

[45] Date of Patent: *Nov. 12, 1996

[54] USE OF AMIDOAMINES IN OPHTHALMIC COMPOSITIONS

[75] Inventors: Nissanke L. Dassanayake, Arlington; Ronald L. Schlitzer, Fort Worth; Joonsup Park, Arlington, all of Tex.

[73] Assignee: Alcon Laboratories, Inc., Fort Worth, Tex.

[*] Notice: The term of this patent shall not extend beyond the expiration date of Pat. No. 5,393,491.

[21] Appl. No.: 395,017

[22] Filed: Feb. 27, 1995

Related U.S. Application Data

[63] Continuation-in-part of Ser. No. 381,889, Feb. 24, 1995, which is a continuation-in-part of Ser. No. 125,629, Sep. 22, 1993, Pat. No. 5,393,491.

[51] Int. Cl.$^6$ .............................. A01N 33/02; A61L 2/18; C11D 3/30; A61K 31/13
[52] U.S. Cl. ...................... 422/28; 424/78.04; 514/840; 510/112
[58] Field of Search ................... 422/28; 514/839, 514/840; 424/78.04; 252/546

[56] References Cited

U.S. PATENT DOCUMENTS

| | | | |
|---|---|---|---|
| 4,013,576 | 3/1977 | Loshaek | 422/28 X |
| 4,185,098 | 1/1980 | Cuntze et al. | 424/199 |
| 4,407,791 | 10/1983 | Stark | 424/80 |
| 4,738,790 | 4/1988 | Miyajima et al. | 252/105 |
| 5,215,976 | 6/1993 | Fost et al. | 514/114 |
| 5,225,055 | 7/1993 | Sibley et al. | 422/22 X |
| 5,393,491 | 2/1995 | Dassanayake et al. | 422/28 |
| 5,415,837 | 5/1995 | Schäfer et al. | 422/28 |

FOREIGN PATENT DOCUMENTS 2616713  11/1977  Germany .

OTHER PUBLICATIONS

Muzyczko, T. M., et al., "Fatty Amidoamine Derivatives: N,N–Dimethyl–N–(3–alkylamidopropyl)amines and Their Salts," *Journal of the American Oil Chemists' Society*, vol. 45, No. 11, pp. 720–725 (1968).

Devinsky, F., et al., "N–(dimethyl)ammino) alkyldodecanamides", *Chemical Abstracts*, vol. 105, No. 23, Dec. 8, 1986, abstract No. 208483.

Limanov, V., et al., "Synthesis and bactericidal activity of quaternary (N–acylaminoproyl) ammonium salts", *Chemical Abstracts*, vol. 95, No. 7, pp. 28–30, Aug. 1981, abstract No. 61431.

Block, Seymour S. *Disinfection, Sterilization, and Preservation*, 4th ed, 1991. p. 232.

*Primary Examiner*—Robert J. Warden
*Assistant Examiner*—E. Leigh Dawson
*Attorney, Agent, or Firm*—James A. Arno; Gregg C. Brown

[57] ABSTRACT

The use of certain amidoamines to disinfect contact lenses and preserve ophthalmic compositions is described, Ophthalmic compositions containing these compounds as disinfecting agents or preservatives are also described, The amidoamines utilized in the present invention have potent antibacterial and antifungal activity, and are chemically compatible with inorganic ions and other materials utilized in ophthalmic compositions.

24 Claims, No Drawings

USE OF AMIDOAMINES IN OPHTHALMIC COMPOSITIONS

CROSS REFERENCE TO RELATED APPLICATIONS

The present application is a continuation-in-part of U.S. patent application Ser. No. 08/381,889, filed Feb. 24, 1995, which is a continuation-in-part of U.S. patent application Ser. No. 08/125,629, filed Sep. 22, 1993, now U.S. Pat. No. 5,393,491.

BACKGROUND OF THE INVENTION

The present invention relates to the field of ophthalmology. More particularly, the invention is directed to compositions and methods for disinfecting contact lenses, and to the chemical preservation of various types of ophthalmic products.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from more discomfort when the lenses are being worn to serious ocular infections. Ocular infections caused by particularly virulent microbes, such as *Pseudomonas aeruginosa*, can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). Moreover, the chemical agents utilized in the currently marketed contact lens disinfection systems generally have limited antifungal activity. Also, many of the chemical agents currently utilized may interact with contact lens materials and/or cause irritation in some individuals. There is, therefore, a particular need in the fields of contact lens disinfection and ophthalmic composition preservation for safe and effective chemical agents having better antifungal activity. The present invention is directed to satisfaction of the above-cited needs.

SUMMARY OF THE INVENTION

The present invention is directed to methods of using certain amidoamines to disinfect contact lenses and to preserve ophthalmic compositions. The invention is also directed to contact lens disinfecting compositions which contain one or more of the subject compounds, and to various types of ophthalmic compositions (e.g., pharmaceuticals, artificial tears and comfort drops) which contain the compounds for purposes of preserving the compositions against microbial contamination.

In addition to having antimicrobial activity, including both antibacterial and antifungal activity, the compounds of the present invention are also surface active. As a result, the compounds also help to clean contact lenses by facilitating the removal of deposits from the lenses.

The amidoamines of the present invention retain their antimicrobial activity in the presence of $Na^+$, $Ca^{++}$, $Cl^-$ and other inorganic ions produced by the dissociation of alkaline and alkaline earth metal salts (e.g., sodium chloride and calcium chloride), and are compatible with polymers and surfactants frequently used in ophthalmic products, such as polyvinylpyrrolidone, and polyoxyethylene/polyoxypropylene copolymers of ethylene diamines. These properties represent significant advantages, relative to many of the antimicrobial agents previously used in the ophthalmic field.

DESCRIPTION OF PREFERRED EMBODIMENTS

The compounds used in the present invention comprise one or more compounds of the following formula, or pharmaceutically acceptable salts thereof (e.g., hydrohalide salts):

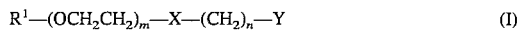

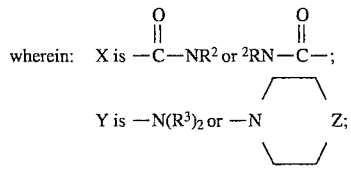

Z is oxygen or $NR^4$;

$R^1$ is $C_6$–$C_{18}$ saturated or unsaturated alkyl, alkylaryl, or alkoxyaryl;

m is 0 to 16;

n is 2 to 16;

$R^2$, $R^3$, and $R^4$ are independently hydrogen, $C_1$–$C_8$ saturated or unsaturated alkyl or hydroxyalkyl, or a pharmaceutically acceptable salt thereof.

The compounds wherein m is 0 to 5, n is 2 to 4, $R^2$ is hydrogen or methyl, $R^3$ is methyl or ethyl, and $R^4$ is hydrogen, methyl or hydroxyethyl are particularly preferred, as are the compounds of Table 1:

TABLE 1

| COMPD. NO. | $R^1$ | m | n | X | $R^2$ | Y | $R^3$ | Z | $R^4$ |
|---|---|---|---|---|---|---|---|---|---|
| 1 | $C_{17}$ | 0 | 3 | $CONR^2$ | H | $N(R^3)_2$ | $CH_3$ | — | — |
| 2 | $C_{13}$ | 0 | 2 | $CONR^2$ | H | $N(R^3)_2$ | $CH_3$ | — | — |
| 3 | $C_{13}$ | 0 | 2 | $CONR^2$ | H | $N(R^3)_2$ | $C_2H_5$ | — | — |
| 4 | $C_{13}$ | 0 | 3 | $CONR^2$ | H | $N(R^3)_2$ | $CH_3$ | — | — |
| 5 | $C_{11}$ | 0 | 3 | $CONR^2$ | H | $N(R^3)_2$ | $CH_3$ | — | — |
| 6 | $C_{11}$ | 0 | 3 | $CONR^2$ | H | $N(R^3)_2$ | $C_2H_5$ | — | — |
| 7 | $C_{11}$ | 0 | 3 | $CONR^2$ | H | \-N⟨ ⟩Z\- | — | O | — |
| 8 | $C_{14}$ | 0 | 2 | $R^2NCO$ | H | \-N⟨ ⟩Z\- | — | N | H |
| 9 | $C_{13}$ | 0 | 3 | $CONR^2$ | H | \-N⟨ ⟩Z\- | — | N | $CH_3$ |
| 10 | $C_{13}$ | 0 | 3 | $CONR^2$ | $CH_3$ | $N(R^3)_2$ | $CH_3$ | — | — |
| 11 | $C_{13}$ | 0 | 3 | $CONR^2$ | H | \-N⟨ ⟩Z\- | — | N | $C_2H_4OH$ |
| 12 | $C_{12}$ | 5 | 3 | $CONR^2$ | H | $N(R^3)_2$ | $CH_3$ | — | — |
| 13 | $C_{12}$ | 4 | 2 | $R^2NCO$ | H | $N(R^3)_2$ | $CH_3$ | — | — |
| 14 | $C_{12}$ | 0 | 3 | $CONR^2$ | H | $N(R^3)_2$ | $CH_3$ | — | — |
| 15 | $C_{11}$ | 0 | 3 | $CONR^2$ | $CH_3$ | $N(R^3)_2$ | $CH_3$ | — | — |
| 16 | $C_{11}$ | 0 | 3 | $CONR^2$ | H | \-N⟨ ⟩Z\- | — | N | $C_2H_4OH$ |
| 17 | $C_{13}$ | 0 | 3 | $CONR^2$ | H | \-N⟨ ⟩Z\- | — | O | — |

The most preferred compound is Compound No. 4, which is known as N,N-Dimethyl-N'-tetradecanoyl-1,3-propylenediamine.

Some of the compounds of the present invention are available from commercial sources. For example, Compound No. 4 is available as MIRISTOCOR®, myristamidopropyl dimethylamine phosphate, from Hoffman-La Roche Inc., Nutley, N.J. (USA), and as Schercodine M from Scher Chemicals Inc., Clifton, N.J. (USA); Compound No. 5 is available as LEXAMINE® L-13, lauramidopropyl dimethylamine, from Inolex Chemical Company, Philadelphia, Pa. (USA); and Compound No. 1 is available as LEXAMINE® S-13, stearamidopropyl dimethylamine, also from Inolex Chemical Company.

The compounds of the present invention can be synthesized in accordance with the following two reaction schemes:

SCHEME I

The following reaction scheme may be utilized to synthesize compounds wherein X is $CONR^2$:

Scheme I:
The following reaction scheme may be utilized to synthesize compounds wherein X is $CONR^2$:

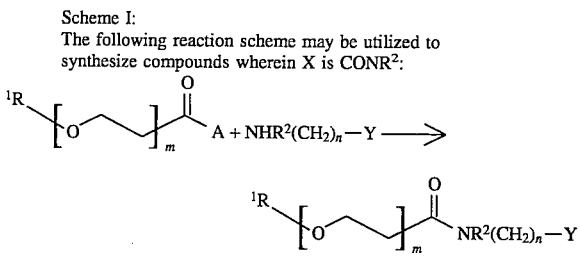

In the foregoing reaction scheme, A is a good leaving group, such as chloride or N-hydroxysuccinimide.

SCHEME II

The following reaction scheme may be utilized to synthesize compounds wherein X is $NR^2CO$:

Scheme II:
The following reaction scheme may be utilized to synthesize compounds wherein X is NR²CO:

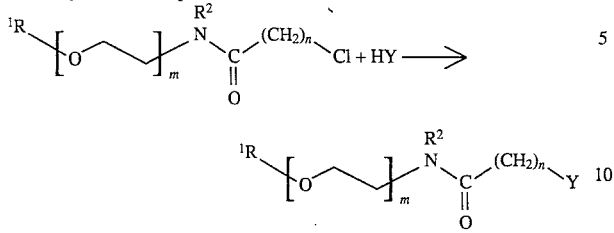

The following article may be referred to for further details concerning the Scheme I synthesis of the amidoamines of formula (I): Muzyczko, et al., "Fatty Amidoamine Derivatives: N,N-Dimethyl-N-(3-alkylamidopropyl)amines and Their Salts", *Journal of the American Oil Chemists' Society*, volume 45, number 11, pages 720–725 (1968). The entire contents of the above-cited article are hereby incorporated in the present specification by reference. The above-cited article does not describe the use of compounds of formula (I) as disinfectants or preservatives in ophthalmic products, particularly products used in the care of contact lenses.

The compounds of formula (I) can be used individually, in combination with one or more other compounds of formula (I), or in combination with other disinfectants or preservatives. The compounds may, for example, be used in combination with the polymeric quaternary ammonium compounds described in U.S. Pat. No. 4,407,791; the entire contents of that patent are hereby incorporated in the present specification by reference. As described in the '791 patent, those polymeric quaternary ammonium compounds are useful in disinfecting contact lenses and preserving ophthalmic compositions. The most preferred polymeric quaternary ammonium compound is polyquaternium-1, which is also known as Onamer-M™ (trademark of Onyx Chemical Company) and Polyquad® (registered trademark of Alcon Laboratories, Inc.). The amount of polyquaternium-1 utilized will generally be in the range of from about 0.00005 to about 0.01 percent by weight, based on the total weight of the composition ("wt. %").

The amount of each compound used will depend on the purpose of the use, e.g., disinfection of contact lenses or preservation of ophthalmic products, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.00005 to about 0.1 wt. %. The concentrations used for preservation will generally be in the range of from about 0.00001 to about 0.05 wt. %.

The compounds of formula (I) may be included in various types of ophthalmic compositions as preservatives, so as to prevent microbial contamination of the compositions. The types of compositions which may be preserved by the compounds of formula (I) include: ophthalmic pharmaceutical compositions, such as topical compositions used in the treatment of glaucoma, infections, allergies or intimation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyoxyethylene/polyoxypropylene copolymers, such as Poloxamine™), viscosity adjusting agents (e.g., hydroxypropyl methyl cellulose and other cellulose derivatives) and buffering agents (e.g., borates, citrates, phosphates and carbonates). The present invention is not limited with respect to the types of ophthalmic compositions in which the compounds of formula (I) may be contained as preservatives. In fact, as already noted above, the compatibility of the compounds of formula (I) with other ingredients of ophthalmic compositions, such as inorganic ions, polymers and surfactants, is a distinct advantage of the present invention, relative to antimicrobial agents previously utilized in the ophthalmic field.

As with the ophthalmic compositions of the present invention which contain one or more compounds of formula (I) as preservatives, the form of the compositions of the present invention containing one or more of the compounds for purposes of disinfecting contact lenses is not limited. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above. The chemical compatibility of the compounds of formula (I) is also a significant advantage with respect to the use of these compounds in the contact lens disinfecting compositions of the present invention.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compounds of formula (I) also have surface active properties. As a result of these properties, the compounds are also useful in cleaning contact lenses. More specifically, the surfactant properties of the compounds facilitate the removal of deposits typically accumulated on contact lenses when worn by human patients. These deposits vary from patient to patient, but will typically include proteins, lipiris, polysaccharides and mixtures thereof, as well as various other soils which may accumulate on the lenses during normal wear and handling. The compounds will exhibit some cleaning effect even at the relatively low concentrations required for purposes of preserving ophthalmic compositions or disinfecting contact lenses. This cleaning effect is therefore useful as a supplement to the effect of other cleaning agents which may be contained in the compositions, such as anionic or nonionic surfactants. Moreover, when used at a concentration of 0.01 wt. % or higher, the compounds exhibit a more pronounced cleaning effect. The manner in which the cleaning effect of the compounds of formula (I) is utilized will depend on the type of contact lens being treated, the severity and type of the deposits on the lenses, and the overall treatment regimen used by the patient. The selection of other components for inclusion in the contact lens cleaning compositions of the present invention will also depend on these factors. The cleaning compositions will generally contain one or more of the compounds of formula (I) in an amount of at least 0.01 wt. %, and preferably from about 0.01 to 1.0 wt. %.

The above-described compositions may be used to clean contact lenses in accordance with known processes, For example, the lenses, after first being removed from the eye and preferably also rinsed, may be lightly rubbed with a small amount of the compositions between the fingers, or may be immersed in a somewhat larger volume of the compositions and then allowed to soak. The lenses are then rinsed and disinfected before being replaced in the eyes of the patients.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition near to 300 milliosmoles. The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention may be used in conjunction with various types of contact lenses, including both lenses generally classified as "hard" and lenses generally classified as "soft".

The following examples are presented to further illustrate methods of synthesizing the amidoamines of the present invention:

EXAMPLE 1

N,N-Dimethyl-N'-Dodecanoyl-1,3-Propylenediamine
(Compound No. 5)

A 500 ml RB flask containing a solution of lauroyl chloride (19.38 g., 89 mM) in dry chloroform (200 ml) was cooled to 0° C. on an ice bath. A solution of N,N-dimethyl-1,3-propanediamine (10.40 g., 51 mM) and triethylamine (9.40 g., 93 mM) in dry chloroform (25 ml) was added dropwise to the cold solution through an addition funnel, then allowed to warm to room temperature and stirred for 2 hours. The chloroform was removed under reduced pressure and the residue redissolved in an ethanol/water mixture (1:1) and neutralized with sodium bicarbonate, followed by extraction with chloroform (4×50 ml). The combined extracts were dried ($MgSO_4$), concentrated, and the residue distilled under reduced pressure (bp 171° C., 10 μ) to give 23.92 g. (68%) of the subject compound as an amber solid.

$^1$H NMR (200 MHz, $CDCl_3$): δ3.33 (q, 2 H,NH—C$\underline{H}_2$), 3.37 (t, 2H, C$\underline{H}_2$N($CH_3$)$_2$), 2.23 (s, 6 H,N($CH_3$)$_2$), 2.15 (t, 2 H, $CH_2$CO), 1.62 (m, 4 H, C$\underline{H}_2$$CH_2$CO, C$\underline{H}_2$$CH_2$N($CH_3$)$_2$), 1.26 (s, 16 H, —$CH_2$—), 0.88 (t, 3 H). Analysis: Calculated for $C_{17}H_{36}N_2O$: C, 71.77; H, 12.75; N, 9.85. Found: C, 72.06; H, 12.76; N, 9.94. IR (neat): 3280, 2910, 2840, 2800, 2750, 1460, 1370, 1260, 1125, 1035 $cm^{-1}$.

EXAMPLE 2

N,N-Dimethyl-N'-Tetradecanoyl-1,3-Propylenediamine
(Compound No. 4)

2.0 g. (0.0196 moles) of 3-dimethylaminopropylamine in 40 ml chloroform was added dropwise to an ice cold chloroform solution (50 ml) of myristoyl chloride (4.17 g., 0.0169 moles). After addition, the ice bath was removed and the solution was stirred for 2 hours. A 25 ml aqueous sodium bicarbonate solution was added and stirred for 30 minutes. The organic layer was then washed with 30 ml aqueous sodium bicarbonate/sodium chloride solution and dried with magnesium sulfate. The solution was concentrated in vacuo and the amide was recrystallized in ethyl acetate to yield 3.29 g. (0.0105 moles, 62.3%) of the subject compound.

$^1$H NMR (200 MHz, $CDCl_3$): δ6.9 (s, 1H, NH), 3.3 (q, 3H, NHC$\underline{H}_2$), 2.4 (t, 2H, NC$\underline{H}_2$), 2.22 (s, 6H, NC$H_3$), 2.15 (t, 2H, COC$H_2$), 1.7–1.5 (m, 4H, COC$H_2$C$\underline{H}_2$ and NHC$H_2$C$\underline{H}_2$), 1.25 (s, 20H, COC$H_2$$CH_2$(C$\underline{H}_2$)$_{10}$), 0.88 (t, 3H, $CH_3$). Elemental Analysis: Calculated for $C_{19}H_{40}N_2O$ (312.52): C, 73.02; H, 12.90; N, 8.96. Found: C, 72.96; H, 12.92; N, 8.93.

EXAMPLE 3

N,N-Diethyl-N'-Tetradecanoyl-1,2-Ethylenediamine
(Compound No. 3)

8.35 g. (0.072 moles) of diethylethylenediamine in 40 ml chloroform was added dropwise to an ice cold chloroform solution (60 ml) of myristoyl chloride (15.84 g., 0.064 moles). After addition, the ice bath was removed and the solution stirred for 6 hours. The reaction mixture was then stirred with aqueous sodium bicarbonate for 10 minutes and the organic layer was washed with an aqueous sodium bicarbonate/sodium chloride solution. The organic layer was then dried over magnesium sulfate and concentrated in vacuo leaving a white solid. The amide was recrystallized in ethyl acetate, filtered and dried to yield 16.58 g. (0.051 moles, 79.1%) of the subject compound.

$^1$H NMR (200 MHz, $CDCl_3$): δ6.2 (S, 1H, NH), 3.3 (q, 2H, NHC$\underline{H}_2$), 2.6–2.5 (m, 6H, NC$H_2$), 2.2 (t, 2H, COC$H_2$), 1.6 (m, 2H, COC$H_2$C$\underline{H}_2$), 1.25 (s, 20H, COC$H_2$$CH_2$(C$\underline{H}_2$)$_{10}$), 1.03 (t, 6H, NC$H_2$$CH_2$$CH_3$), 0.88 (t, 3H, $CH_3$). Elemental Analysis: Calculated for $C_{20}H_{42}N_2O$ (326.54): C, 73.56; H, 12.96; N, 8.58 Found: C, 73.44; H, 12.97; N, 8.56.

EXAMPLE 4

N,N-Diethyl-N'-Dodecanoyl-1,3-Propylenediamine
(Compound No. 6)

A 500 ml RB flask containing a solution of lauroyl chloride (19.03 g., 87 mM) in dry chloroform (200 ml) was cooled to 0° C. on an ice bath. A solution of N, N-diethyl-1,3-propanediamine (15.00 g., 115 mM) in dry chloroform (25 ml) was added dropwise to the cold solution then allowed, to warm to room temperature and stirred for 2 hours. The chloroform was removed under reduced pressure and the residue redissolved in an ethanol/water mixture (1:1) and neutralized with sodium bicarbonate, followed by extraction with chloroform (4×50 ml). The combined extracts were dried (MgSO4), concentrated, and the residue distilled under reduced pressure (bp 176° C., 20 μ) to give 21.47 g. (79%) of the subject compound as an amber oil.

$^1$H NMR (200 MHz. $CDCl_3$): δ3.33 (q, 2 H,NH—C$\underline{H}_2$), 2.52 (m, 6 H, C$\underline{H}_2$N(C$\underline{H}_2$$CH_3$)$_2$), 2.15 (t, $CH_2$CO), 1.63 (m, 4 H, C$\underline{H}_2$$CH_2$CO, C$\underline{H}_2$$CH_2$N($CH_2$$CH_3$)$_2$), 1.25 (s, 16 H, —$CH_2$—), 1.04 (t, 6 H, N($CH_2$C$\underline{H}_3$), 0.88 (t, 3 H, —$CH_3$). IR (neat): 3280, 3080, 2910, 2840, 2800, 2750, 1640, 1550, 1460, 1370, 1280, 1100, 1060 $cm^{-1}$ MS (Cl): m/e 313 ($MH^+$).

EXAMPLE 5

N-Tetradecyl-3-(1-piperazino) propionamide (Compound No. 8)

10.6 g. (0.0835 mol) of 3-chloropropionyl chloride in 50 mL chloroform was added dropwise to an ice cold 100 mL chloroform solution containing 14.4 g. (0.0815 mol) of tetradecylamine and 11.3 g. (0.112 mol) of triethylamine. The reaction mixture was stirred for three hours and washed with 3×75 mL, cold aqueous acidic sodium chloride followed by 75 mL cold aqueous sodium chloride. The chloroform layer was dried ($MgSO_4$) and concentrated in vacuo resulting in a solid which was crystallized successively from ethyl acetate to yield 18.22 g. (73.6%) of the chloropropionyl amide.

7.6 g. (0.025 mol) of the amide intermediate was reacted with 21.6 g. (0.25 mol) of piperazine in 25 mL dimethylsulfoxide at 125° C. for four hours. This reaction mixture was treated with 200 mL of ice cold aqueous sodium bicarbonate containing sodium chloride, and was then extracted with 3 ×70 mL chloroform. The combined chloroform layers were washed with aqueous sodium chloride (4×225 mL), dried ($MgSO_4$), filtered, concentrated in vacuo and dried at 80° C. under high vacuum to yield a white precipitate. The precipitate was crystallized successively from ethyl acetate to yield 3.0 g. (32.0%) of the subject compound.

$^1$H NMR ($CDCl_3$): δ3.2–3.3 (q, 2H, $CH_3CH_2)_{11}CH_2C\underline{H}_2$),2.9 (t, 4H, piperazine), 2.6 (t, 2H, C(=O)$CH_2$), 2.5 (m, 4H, piperazine), 2.4 (t, 2H, C(=O)$CH_2C\underline{H}_2$), 1.5 (m, 2H, $CH_3(CH_2)_{11}C\underline{H}_2$), 1.25 (broad s, 22H, $CH_3(C\underline{H}_2)_{11}$), and 0.88 (t, 3H, $CH_3$).

Elemental Analysis: Calculated for $C_{21}H_{43}N_3O$(M.W. 353.57): C, 71.33; H,12.25; N, 11.88. Found: C, 71.26; H, 12.20; N, 11.86.

EXAMPLE 6

3-Dimethylamino-N-(3,6,9,12-tetraoxa-tetracosyl) propionamide (Compound No. 13)

A 60 mL chloroform solution containing 3.7 g. (0.0102 mol) of $C_{12}(PEO)_4NH_2$ (prepared by reaction of polyoxyethylene-4-lauryl ether with thionyl chloride followed by reaction with potassium phthalimide and then deprotection by hydrazine) and 2.25 g. (0.017 mol) of N,N-diisopropylethylamine, was added dropwise to an ice cold 50 mL chloroform solution containing 1.88 g. (0.0148 mol) of 3-chloropropionyl chloride. The reaction mixture was stirred for two hours, washed with aqueous HCl (1×150 mL) and aqueous sodium chloride (2×75 ml) successively, dried ($MgSO_4$), filtered and concentrated in vacuo to yield 3.72 g. (80.7%) of the chloropropionyl intermediate.

A 50 mL tetrahydrofuran solution of 2.72 g. (0.006 mol) of the chloropropionyl intermediate was reacted with an excess amount of dimethylamine at 80° C. overnight. The reaction mixture was concentrated in vacuo, dissolved in 50 mL of chloroform and washed with an aqueous sodium chloride containing sodium bicarbonate solution (3×10 mL). The organic layer was dried ($MgSO_4$), filtered, and concentrated in vacuo. This material was purified by ion exchange chromatography to yield 0.35 g. (12.7%) of the subject compound.

$^1$H NMR ($CDCl_3$): δ8.2 (broad, 1H, NH), 3.6–3.4 (broad, 18H, PEO), 2.6 (app t, 2H, C (=O)$CH_2$), 2.3 (app t, 2H, $NCH_2$), 2.2 (s, 6H, $N(CH_3)_2$), 1.5 (m, 2H, $(CH_2)_9C\underline{H}_2$), 1.2 (broad s, 18H, $(C\underline{H}_2)_9$) and 0.8 (app t, 3H, $CH_3$).

Elemental Analysis: Calculated for $C_{27}H_{56}N_2O_6·\frac{1}{2}H_2O$ (MW 513.76) C,63.12; H, 11.18; N, 5.45. Found: C, 62.77; H, 10.92; N, 4.82.

EXAMPLE 7

N,N-Dimethyl-N'-(3,6,9,12,15-pentaoxa-heptacosanoyl)-1,3-propylenediamine (Compound No. 12)

A mixture of 4.4 g. (0.0104 mol) of $C_{12}(PEO)_4OCH_2COOH$ (made from carboxymethylation of polyoxyethylene-4-lauryl ether with sodium hydroxide and sodium chloroacetate) and 1.26 g. (0.011 mol) of N-hydroxysuccinimide was reacted with 2.31 g. (0.0112 mol) of dicyclohexylcarbodiimide in an ice bath, under argon for four hours. The reaction mixture was treated with acetic acid several times, filtered and concentrated in vacuo to yield 5 g. (86%) of the activated ester.

An ice cold 20 mL ethyl acetate solution of 5 g. (0.009 mol) of the activated intermediate was reacted with 1.86 g. (0.0182 mol) of N,N-dimethylpropylenediamine for one hour, and then for another two hours at room temperature. The solution was then diluted with 60 mL of ethyl acetate and washed with aqueous sodium chloride (3×10 mL). The organic layer was concentrated in vacuo, re-dissolved in ethyl acetate, filtered, concentrated in vacuo and dried on the vacuum pump to yield 3.68 g. (72.0%) of the subject compound.

$^1$H NMR ($CDCl_3$): δ7.5 (broad, 1H, NH), 4.0 (s, 2H, C(=O)$CH_2$), 3.6 (broad, 18H, PEO), 3.4 (t, 2H, C(=O)$CH_2OC\underline{H}_2$), 3.3 (q, 2H, $NHCH_2$), 2.3 (t, 2H, $NCH_2$), 2.2 (s, 6H, $N(CH_3)_2$), 1.7 (m, 2H, $NHCH_2CH_2$), 1.6 (m, 2H, $CH_2$), 1.3 (broad s, 18H, $(CH_2)_9$), and 0.9 (t, 3H, $CH_3$).

Elemental Analysis: Calculated for $C_{28}H_{58}N_2O_{6.5}$ (MW 526.78): C, 63.84; H, 11.10; N, 5.32. Found: C, 63.89; H, 11.01; N, 5.03.

EXAMPLE 8

4-Hydroxyethyl-N-dodecanoyl-1-piperazinepropylamine (Compound No. 16)

A 50 mL chloroform solution of 2.45 g. (0.0112 mol) of dodecanoyl chloride was added dropwise under argon to an ice cold 50 mL chloroform solution of 2.12 g. (0.0113 mol) of N-(3-aminopropyl)-N'-(2-hydroxyethyl) piperazine and stirred for one hour maintaining the temperature between 2°–4° C. This reaction mixture was then treated with 100 mL of aqueous sodium bicarbonate and extracted with chloroform (2×50 mL). The combined chloroform layers were washed with aqueous sodium bicarbonate (2×50 mL), dried ($MgSO_4$), filtered, and concentrated in vacuo. The remaining solid was crystallized in ethyl acetate/hexane to yield 1.69 g. (40.8%)of the subject product.

$^1$H NMR ($CDCl_3$): δ3.6 (t, 2H, $HOC\underline{H}_2$), 3.3–3.4 (q, 2H, $NHC\underline{H}_2$) , 2.4–2.7 (m, 12H, $HOCH_2C\underline{H}_2$, $NHCH_2CH_2C\underline{H}_2$, piperazine), 2.1–2.2 (t, 2H, C(=O)$CH_2$) ,1.5–1.7 (m, 4H), $(CH_2)_8C\underline{H}_2$, $NHCH_2C\underline{H}_2$), 1.25 (s, 16H, $(C\underline{H}_2)s$), and 0.88 (t, 3H, $C\underline{H}_3$).

Elemental Analysis: Calculated for $C_{21}H_{43}N_3O_2$(MW 369.59): C, 68.25; H, 11.73; N, 11.37. Found: c, 68.15; H, 11.82; N, 11.32.

EXAMPLE 9

N,N-Dimethyl-N'-dodecanoyl-N'-methyl-1,3-propylenediamine (Compound No. 15)

A mixture of 3.89 g. (0.0335 mol) of N,N,N'-trimethyl-1,3-propylenediamine and 4.33 g. (0.0335 mol) of N,N-diisopropylethylamine in 50 mL chloroform was added to 7.33 g. (0.0335 mol) of lauroyl chloride dropwise, on an icebath, and was then reacted for another two hours at room temperature. 75 mL of aqueous sodium bicarbonate was then added to this reaction mixture, and the chloroform layer was separated and washed with 125 mL aqueous sodium bicarbonate followed by 100 mL water. The chloroform layer was then dried (MgSO$_4$) filtered and concentrated in vacuo.

The acidified compound (with hydrochloric acid) was concentrated in vacuo, and then crystallized from acetonitrile to yield 3.04 g. (0.0102 mol, 30.4%) of the subject compound.

$^1$H NMR (CDCl$_3$): δ3.5 (t, 2H, CO-NCH$_2$), 3.1 (S, 3H, N-CH$_3$), 3.0 (t, 2H, N-CH$_2$), 2.8 (s, 6H, N-(CH$_3$)$_2$), 2.3 (t, 2H, CO-CH$_2$), 2.2 (m, 2H, NCH$_2$CH$_2$), 1.6 (m, 2 H, COCH$_2$CH$_2$), 1.3 (broad s, 16H, CH$_2$), and 0.9 (t, 3H, CH$_3$).

Elemental Analysis: Calculated for C$_{18}$H$_{39}$N$_2$OCl·¼H$_2$O (MW 333.47) C, 64.83; H, 11.94; N, 8.40. Found: C, 64.59; H, 11.80; N, 8.27.

EXAMPLE 10

N-N-Dimethyl-N'-dodecanoyl-N'-methyl-1,3-propylenediamine (Compound No. 10)

A mixture of 3.56 g. (0.0306 mol) of N,N,N'-trimethyl-1,3-propanediamine and 3.96 g. (0.0306 mol) of N,N-diisopropylethylamine in 50 mL chloroform, on an ice bath, was added dropwise to 7.55 g. (0.0306 mol) of myristoyl chloride, and then reacted for two hours. The reaction mixture was then treated with 75 mL of aqueous sodium bicarbonate. The separated chloroform layer was washed with aqueous sodium bicarbonate and water successively. The chloroform layer was dried (MgSO$_4$) filtered, and concentrated in vacuo. The acidified (with HCl) compound was crystallized (2×) from acetonitrile to yield 1.00 g. (10%) of the subject compound.

$^1$H NMR (CDCl$_3$): δ3.5 (t, 2H, CO-NCH$_2$), 3.1 (s, 3H, N-CH$_3$), 3.0 (t, 2H, N-CH$_2$), 2.8 (s, 6H, N-(CH$_3$)$_2$), 2.3 (t, 2H, CO-CH$_2$), 2.2 (m, 2H, NCH2CH$_2$), 1.6 (m, 2 H, COCH$_2$CH$_2$), 1.3 (broad s, 20H, CH$_2$), and 0.9 (t, 3H, CH$_3$).

Elemental Analysis: Calculated for C$_{20}$H$_{43}$N$_2$OCl(MW 363.03); C, 66.17; H, 11.94; N, 7.72. Found: c, 65.96; H, 12.00; N, 7.67.

EXAMPLE 11

N,N-Dimethyl-N'-tridecanoyl-1,3-propylenediamine (Compound No. 14)

A mixture of methyl tridecanoate (11.4 g., 0.05 mol) and N,N-dimethylpropyleneamine (7.7 g., 0.05 mol) was reacted at 180° C. for 5 hours with removal of methanol from the reaction mixture and crystallized from acetonitrile to afford 10 g. (66.7%) of the subject compound.

MP: 39°–40° C. $^1$H NMR (CDCl$_3$): δ6.9 (broad, 1H, NH), 3.35 (app. q, 2H, NHCH$_2$), 2.4 (t, 2H, NCH$_2$), 2.2 (s, 3H, N(CH$_3$)$_2$), 1.65 (m, 4H, CH$_2$), 1.3 (app. s, 18H, CH$_2$), 0.9 (t, 3H, CH$_3$).

Elemental Analysis: Calculated for C$_{18}$H$_{38}$N$_2$O (298.51): C, 72.43; H, 12.83; N, 9.38. Found: C, 72.54; H, 12.87; N, 9.40. GC: 99.6%.

EXAMPLE 12

4-Hydroxyethyl-N-tetradecanoyl-1-piperazinepropylamine (Compound No. 11)

A 50 mL chloroform solution of 6.21 g. (0.025 1 mol) of myristoyl chloride was added dropwise under argon to an ice cold 75 mL chloroform solution of 4.79 g. (0.0256 mol) of N-(3-aminopropyl)-N'-(2-hydroxyethyl)piperazine. After stirring for two hours, 100 mL of aqueous sodium carbonate was added and stirred for 30 minutes. The layers were separated and the chloroform layer was washed with aqueous sodium carbonate (2×125 mL) followed by water (2×75 mL). The chloroform layer was concentrated in vacuo and the remaining amber liquid was crystallized successively from ethyl acetate to yield 4.56 g. (45.6%) of the subject compound.

$^1$H NMR (CDCl$_3$): δ3.6 (t, 2H, HOCH$_2$), 3.3–3.4 (q, 2H, NHCH$_2$), 2.4–2.6 (m, 12H, HOCH$_2$CH$_2$, NHCH$_2$CH$_2$H$_2$, piperazine), 2.1 (t, 2H, C(=O)CH$_2$), 1.5–1.7 (m, 4H, CH$_3$(CH$_2$)$_{10}$CH$_2$, NHCH$_2$CH$_2$), 1.25 (broad s, 20H, CH$_3$(CH$_2$)$_{10}$), 0.88 (t, 3H, CH$_3$).

Elemental Analysis: Calculated for C$_{23}$H$_{47}$N$_3$O$_2$·½H$_2$O (MW 406.65): C, 67.93; H, 11.89; N, 10.33. Found: C, 67.84; H, 11.56; N, 10.35.

EXAMPLE 13

4-Methyl-N-tetradecanoyl-1-piperazinepropylamine. (Compound No. 9)

4.7 g. (0.03 mol) of N-methyl-N'-(3-aminopropyl)-piperazine (prepared from N-methyl piperazine and acrylonitrile and subsequent reduction to the primary amine) in 200 mL chloroform was cooled down in an ice bath. To this was added 7.3 g. (0.03 mol) of myristoyl chloride dropwise for two hours. The reaction mixture was brought to room temperature and then allowed to react for another four hours. The reaction mixture was treated with 10 g. of sodium bicarbonate in 100 mL water and the separated chloroform layer was washed with water (2×200 mL). The organic layer was dried (MgSO$_4$), filtered and concentrated in vacuo. Crystallization from acetonitrile afforded 8 g. (72.3%) of the subject product.

MP: 55°–56° C. $^1$H NMR (CDCl$_3$): δ7.1 (broad, 1H NH), 3.35 (app. q, 2H, NHCH$_2$), 2.5 (app t, 8H, piperazine), 2.3 (s, 3H, NCH$_3$), 2.15 (t, 2H, COCH$_2$), 1.65 (m, 4H, CH$_2$), 1.3 (app. s, 22H, CH$_2$), and 0.9 (t, 3H, CH$_3$).

Elemental Analysis: Calculated for C$_{22}$H$_{45}$N$_3$O (M.W. 367.62): C, 71.88; H, 12.34; N, 11.43. Found: C, 71.88; H, 12.10; N, 11.40. GC: 97.3%.

EXAMPLE 14

N-Dodecanoyl-1-morpholinopropylamine (Compound No. 7)

To a 100 mL RB flask equipped with a magnetic stir bar and addition funnel, was added a mixture of 2.00 g. (9.14 mM) of lauroyl chloride in chloroform (50 mL), cooled in an ice bath. Through the addition funnel, a solution of 1.32 g. (9.15 mM) of 4-(3-aminopropyl)imidazole and 1.0 g. (9.9 mM) of triethylamine in chloroform (10 mL), was then added dropwise to the cold, stirred solution. After the addition, the ice bath was removed and the reaction allowed to stir overnight at room temperature. The chloroform was removed by rotary evaporation and the residue redissolved in ethanol/water (1:1). 2 g. (24 mM) of sodium bicarbonate was then added, and the mixture was stirred for several hours. The aqueous mixture was extracted with ethyl acetate (3×50 mL), the combined organic extracts dried (MgSO$_4$), and the filtrate concentrated. The residue was crystallized from hexane/ethyl acetate to afford 1.57 g. (53%) of white crystals of the subject compound.

MP: 52°–54° C. $^1$H NMR (200 MHz, CDCl$_3$): δ7.27 (S, 1H, NH), 3.72 (t, 4H, CH$_2$-O-CH$_2$), 3.34 (t, 2H, C$\underline{H}_2$-NH), 2.46(t, 6H, N(CH$_2$)$_3$), 2.15(t, 2H, CH$_2$,CH$_2$-CO), 1.68(m, 4H, CO-CH$_2$-C$\underline{H}_2$ and N-CH$_2$-C$\underline{H}_2$-CH$_2$-NH), 1.26(s, 16H, CO-CH$_2$-CH$_2$-(C$\underline{H}_2$)$_8$), 0.88(t, 3H, CH$_3$).

Elemental Analysis: Calculated for C$_{19}$H$_{38}$N$_2$O$_2$.0.9H$_2$O (342–72) C, 66.59; H, 11.70; N, 8.17. Found: C, 66.61; H, 11.47; N, 8.03. GC: greater than 99%.

EXAMPLE 15

N-Tetradecanoyl-1-morpholinopropylamine
(Compound No. 17)

To a 100 mL RB flask equipped a with magnetic stir bar and an addition funnel, was added 2.67 g. (10.82 mM) of myristoyl chloride in chloroform (50 mL), cooled in an ice bath. Through the addition funnel a solution of 1.60 g. (11.09 mM) of 4-(3-aminopropyl)imidazole and 1.11 g. (10.97 mM) of triethylamine in chloroform (10 mL) was added dropwise to the cold, stirred solution. After addition, the ice bath was removed and the reaction allowed to stir overnight at room temperature. The chloroform was removed by rotary evaporation and the residue redissolved in ethanol/water (1:1). 2 g. (24 mM) of sodium bicarbonate was added and the mixture was stirred for several hours. The aqueous mixture was extracted with ethyl acetate (3×50 mL), the combined organic extracts dried (MgSO$_4$), and the filtrate concentrated. The residue was crystallized from hexane/ ethyl acetate to afford 3.0 g. (78%) of white crystals of the subject compound.

MP: 62°–64° C. $^1$H NMR (200 MHz, CDCl$_3$): δ7.27 (S, 1H, NH), 3.73 (t, 4H, CH$_2$-O-CH$_2$), 3.36 (q, 2H, C$\underline{H}_2$-NH), 2,46 (t, 6H, N(CH$_2$)$_3$, 2.15 (t, 2H, CH$_2$-CO), 1.68 (m, 4H, CO-CH$_2$-C$\underline{H}_2$ and N-CH$_2$-C$\underline{H}_2$-CH$_2$-NH), 1.26 (s, 20H, CO-CH$_2$-CH$_2$-(C$\underline{H}_2$)$_{10}$), 0.88 (t, 3H, CH$_3$).

Elemental Analysis: Calculated for C$_{21}$H$_{42}$N$_2$O$_2$(354.56) C, 71.14; H, 11.94; N, 7.90. Found: C, 70.86; H, 11.85; N, 7.78. GC: greater than 98%.

The following examples are presented to further illustrate ophthalmic compositions which may contain one or more of the compounds of formula (I):

EXAMPLE 16

The following formulation might serve as a vehicle for an ophthalmic drug. The formulation would contain one or more compounds of formula (I) as a preservative.

| Ingredient | Amount (wt. %) |
|---|---|
| Sodium Chloride | 0.5% |
| Mannitol | 2.5% |
| HEPES | 0.119% |
| NaOH/HCl | pH 7.0 |
| Purified water | QS 100 |

EXAMPLE 17

The following formulation may be utilized as a contact lens disinfecting solution. The formulation would contain one or more compounds of formula (I) as a disinfectant.

| Ingredient | Amount (wt. %) |
|---|---|
| Mannitol | 0.64% (w/v) |
| Boric Acid | 0.225% |
| Sodium Borate | 0.08% |
| Sodium Citrate | 0.46% |
| Citric Acid | 0.016% |
| Sodium Chloride | 0.48% |
| Disodium Edetate | 0.05% |
| NaOH/HCl | pH 7.0 |
| Purified Water | QS 100 |

EXAMPLE 18

The following formulation, which would contain one or more compounds of formula (I), may be utilized as a contact lens disinfecting solution, and would also aid in the cleaning of the lens.

| Ingredient | Amount (wt. %) |
|---|---|
| Boric Acid | 0.58% |
| Sodium Borate | 0.18% |
| Sodium Chloride | 0.49% |
| Disodium Edetate | 0.05% |
| Poloxamine ™ | 0.1% |
| Polyquaternium-1 | 0.001% |
| NaOH/HCl | pH 7.0 |
| Purified Water | QS 100% |

What is claimed is:

1. A preserved pharmaceutical composition comprising an aqueous ophthalmic composition and 0.00001 to 0.05 wt. % of a compound of the following formula to preserve said ophthalmic composition from microbial contamination:

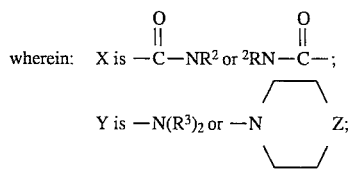

Z is oxygen or NR$^4$;

R$^1$ is C$_6$–C$_{18}$ saturated or unsaturated alkyl, alkylaryl, or alkoxyaryl;

m is zero to 16;

n is 2 to 16;

R$^2$, R$^3$, and R$^4$ are independently hydrogen, C$_1$–C$_8$ saturated or unsaturated alkyl or hydroxyalkyl, or a pharmaceutically acceptable salt thereof.

2. A composition according to claim 1, wherein n is 2 to 4, and m is 0 to 5.

3. A composition according to claim 2, wherein R$^2$ is hydrogen or methyl, and R$^3$, if present, is methyl or ethyl.

4. A composition according to claim 1, wherein R$^1$ is heptadec-8-enyl, undecyl, undecenyl, dodecyl, tridecyl, tetradecyl, pentadecyl or heptadecyl, R$^2$ is hydrogen or methyl, R$^3$, if present, is methyl or ethyl, and R$^4$, if present, is hydrogen, methyl or hydroxyethyl.

5. A composition according to claim 1, wherein $R^1$ is tridecyl, m is 0, n is 3, Y is $N(R^3)_2$ and $R^3$ is methyl.

6. An ophthalmic composition for disinfecting contact lenses, comprising 0.00005 to 0.1 wt. % of a compound of the following formula:

$$R^1\text{-}(OCH_2CH_2)_m\text{-}X\text{-}(CH_2)_n\text{-}Y \qquad (I)$$

wherein: X is $-\overset{O}{\underset{\|}{C}}-NR^2$ or $^2RN-\overset{O}{\underset{\|}{C}}-$;

Y is $-N(R^3)_2$ or $-N\overbrace{\phantom{xxx}}Z$;

Z is oxygen or $NR^4$;

$R^1$ is $C_6$–$C_{18}$ saturated or unsaturated alkyl, alkylaryl, or alkoxyaryl;

m is zero to 16;

n is 2 to 16;

$R^2$, $R^3$, and $R^4$ are independently hydrogen, $C_1$–$C_8$ saturated or unsaturated alkyl or hydroxyalkyl, or a pharmaceutically acceptable salt thereof.

7. A composition according to claim 6, wherein n is 2 to 4, and m is 0 to 5.

8. A composition according to claim 7, wherein $R^2$ is hydrogen or methyl, and $R^3$, if present, is methyl or ethyl.

9. A composition according to claim 6, wherein $R^1$ is heptadec-8-enyl, undecyl, undecenyl, dodecyl, tridecyl, tetradecyl, pentadecyl or heptadecyl, $R^2$ is hydrogen or methyl, $R^3$, if present, is methyl or ethyl, and $R^4$, if present, is hydrogen, methyl or hydroxyethyl.

10. A composition according to claim 6, wherein $R^1$ is tridecyl, m is 0, n is 3, Y is $N(R^3)_2$ and $R^3$ is methyl.

11. A composition according to claim 6, wherein the composition further comprises 0.00005 to 0.01 wt. % of polyquaternium-1.

12. A method of disinfecting a contact lens which comprises immersing the lens in an antimicrobial composition for a time sufficient to disinfect the lens, said composition comprising 0.00005 to 0.1 wt. % of a compound of the following formula:

$$R^1\text{-}(OCH_2CH_2)_m\text{-}X\text{-}(CH_2)_n\text{-}Y \qquad (I)$$

wherein: X is $-\overset{O}{\underset{\|}{C}}-NR^2$ or $^2RN-\overset{O}{\underset{\|}{C}}-$;

Y is $-N(R^3)_2$ or $-N\overbrace{\phantom{xxx}}Z$;

Z is oxygen or $NR^4$;

$R^1$ is $C_6$–$C_{18}$ saturated or unsaturated alkyl, alkylaryl, or alkoxyaryl;

m is zero to 16;

n is 2 to 16;

$R^2$, $R^3$, and $R^4$ are independently hydrogen, $C_1$–$C_8$ saturated or unsaturated alkyl or hydroxyalkyl, or a pharmaceutically acceptable salt thereof.

13. A method according to claim 12, wherein n is 2 to 4, and m is 0 to 5.

14. A method according to claim 13, wherein $R^2$ is hydrogen or methyl, and $R^3$, if present, is methyl or ethyl.

15. A method according to claim 12, wherein $R^1$ is heptadec-8-enyl, undecyl, undecenyl, dodecyl, tridecyl, tetradecyl, pentadecyl or heptadecyl, $R^2$ is hydrogen or methyl, $R^3$, if present, is methyl or ethyl, and $R^4$, if present, is hydrogen, methyl or hydroxyethyl.

16. A method according to claim 12, wherein $R^1$ is tridecyl, m is 0, n is 3, Y is $N(R^3)_2$ and $R^3$ is methyl.

17. A method according to claim 12, wherein the composition further comprises 0.00005 to 0.01 wt. % of polyquaternium-1.

18. A method of preserving an ophthalmic composition which comprises including in the composition 0.00001 to 0.05 wt. % of a compound of the following formula to preserve the composition from microbial contamination:

$$R^1\text{-}(OCH_2CH_2)_m\text{-}X\text{-}(CH_2)_n\text{-}Y \qquad (I)$$

wherein: X is $-\overset{O}{\underset{\|}{C}}-NR^2$ or $^2RN-\overset{O}{\underset{\|}{C}}-$;

Y is $-N(R^3)_2$ or $-N\overbrace{\phantom{xxx}}Z$;

Z is oxygen or $NR^4$;

$R^1$ is $C_6$–$C_{18}$ saturated or unsaturated alkyl, alkylaryl, or alkoxyaryl;

m is zero to 16;

n is 2 to 16;

$R^2$, $R^3$, and $R^4$ are independently hydrogen, $C_1$–$C_8$ saturated or unsaturated alkyl or hydroxyalkyl, or a pharmaceutically acceptable salt thereof.

19. A method according to claim 18, wherein n is 2 to 4, and m is 0 to 5.

20. A method according to claim 19, wherein $R^2$ is hydrogen or methyl, and $R^3$, if present, is methyl or ethyl.

21. A method according to claim 18, wherein $R^1$ is heptadec-8-enyl, undecyl, undecenyl, dodecyl, tridecyl, tetradecyl, pentadecyl or heptadecyl, $R^2$ is hydrogen or methyl, $R^3$, if present, is methyl or ethyl, and $R^4$ is hydrogen, methyl or hydroxyethyl.

22. A method according to claim 18, wherein $R^1$ is tridecyl, m is 0, n is 3, Y is $N(R^3)_2$ and $R^3$ is methyl.

23. A method according to claim 18, wherein the composition further comprises 0.00005 to 0.01 wt. % of polyquaternium-1.

24. A method according to claim 23, wherein said composition further comprises a cleaning effective amount of an ophthalmically acceptable surfactant.

\* \* \* \* \*